United States Patent [19]

Vit et al.

[11] Patent Number: 4,693,986

[45] Date of Patent: Sep. 15, 1987

[54] CERAMIC PROCESS AND PRODUCTS

[75] Inventors: Jaroslay Vit, Union, N.J.; Ronald L. Salsbury, Dublin; Don J. Henderson, Danville, both of Calif.

[73] Assignee: Orthomatrix, Inc., Dublin, Calif.

[21] Appl. No.: 9,612

[22] Filed: Jan. 21, 1987

Related U.S. Application Data

[63] Continuation of Ser. No. 748,547, Jun. 25, 1985.

[51] Int. Cl.$^4$ .................. C04B 35/00; C07C 61/06
[52] U.S. Cl. .................................. 501/1; 501/153;
   23/313 R; 264/59; 264/117; 623/16
[58] Field of Search .................... 501/1; 264/117, 121,
   264/59, 63, DIG. 51; 23/313 R; 623/16

[56] References Cited

U.S. PATENT DOCUMENTS

| | | |
|---|---|---|
| 3,027,229 | 3/1962 | Towey et al. |
| 3,030,228 | 4/1962 | Hernandez et al. ............... 264/59 |
| 3,787,900 | 1/1974 | McGee |
| 3,873,327 | 3/1975 | Duff |
| 3,881,911 | 5/1975 | Cheney et al. ............... 75/0.5 BB |
| 4,097,935 | 7/1978 | Jarcho |
| 4,218,255 | 8/1980 | Bajpai et al. ............... 501/153 O R |
| 4,321,224 | 3/1982 | Shimizu et al. ............. 264/DIG. 51 |
| 4,497,075 | 2/1985 | Niwa et al. ....................... 501/1 X |
| 4,508,667 | 4/1985 | Elliot ............................ 264/121 X |
| 4,548,959 | 10/1985 | Nagai et al. ..................... 501/1 X |
| 4,551,436 | 11/1985 | Johnson et al. ............... 501/90 OR |
| 4,629,464 | 12/1986 | Takata et al. ................. 623/160 R |

OTHER PUBLICATIONS

Misiek et al., *Soft Tissue Responses to Hydroxylapatite Particles of Different Shapes*, J Oral Maxiollofac Surg., 42:150–160, 1964.

Rotare, H. M. et al., "Sintered Hydroxyapatite Ceramic for Wear Studies", *J. Dent. Res.* (1978), 777–783.
Rootare, H. M. et al., "Characterization of the Compaction and Sintering of Hydroxyapatite Powders by Mercury Porosimetry", *Powder Technology*, 9, pp. 192–211.
Kutty T. R. N., title Indian J. Chem., vol. 11, (July, 1973), 695–697.
Hayek, et al. Inorganic Synthesis 7, (1963) 63–65.
Monroe, et al., J. Dent. Res 580, 860 (1974).
Della, M. R., et al., "Hydroxyapatite formed from Coral Skeletal Carbonate by Hydrothermal Exchange", Nature 247, 220 (1974).
Rao, R. W., et al. title J. Dent. Res. 53, 1351 (1974).
Dennisen, H. W. et al. "Hydroxylapatite Implants: Preparation and Use in Alveolar Ridge Preservation".
Jervoe, P. et al., Acta Chem. Scand. A 28 447–481 (1974).
Krjewski, A., et al., Biomaterials, vol. 2 (1981), 105–111.
Denissen, H. W. et al., Mechanical Properties of Biomaterials, Wiley & Sons (1980) 489–505.
Krajewski, A., et al., "The Behavior of Apatite-Based Ceramics in Relation to the Critical 1150°–1250° C. Temperatures Range", Butterworth & Co. (1984).
Bigi, A., et al., ICI Business Press (1980) "Characterization of Synthetic Apatites for Bioceramic Implants".

*Primary Examiner*—William R. Dixon, Jr.
*Assistant Examiner*—Karl Group
*Attorney, Agent, or Firm*—Vidas & Arrett

[57] ABSTRACT

The invention disclosed by this application relates to a novel method of processing sinterable powders into sintered ceramic products. This application also relates to novel forms of aluminum oxide, hydroxylapatite, and tricalcium phosphate ceramic products prepared in accordance with the method of this invention, as well as novel intermediate products useful to prepare the novel ceramic products of this invention.

16 Claims, No Drawings

CERAMIC PROCESS AND PRODUCTS

This is a continuation of co-pending application Ser. No. 748,547 filed on June 25, 1985.

FIELD OF THE INVENTION

The invention disclosed by this application relates to a novel method of processing sinterable powders into sintered ceramic products. This application also relates to novel forms of aluminum oxide, hydroxylapatite, and tricalcium phosphate ceramic products prepared in accordance with the method of this invention, as well as novel intermediate products useful to prepare the novel ceramic products of this invention.

BACKGROUND OF THE INVENTION

Bone prostheses are often needed for temporary or permanent use in man or animals. A wide variety of different biocompatible materials have been developed for use as bone prostheses, including, for example, natural or synthetic mineral materials, metals, such as Vitallium TM, stainless steel and chromium alloys, as well as organic resins, such as silicone rubbers. The foregoing materials may be employed, for example to: (1) replace a portion of bone which has been lost due to accident or disease, or (2) reinforce a portion of bone which has atrophied or suffered a reduction in mineral content.

In some individuals the alveolar ridge becomes abnormally thin and unable to support either natural or artificial teeth. The support or rebuilding of the alveolar ridge has, therefore, become an important step in the treatment of those individuals suffering from a weakening in the alveolar ridge due to periodontal disease or other causes. Mineral materials of both synthetic and natural origins have been employed for bone restorative purposes in the alveolar ridge and, hence, to prevent tooth loss due to bone loss in the alveolar ridge.

Many of the same synthetic and naturally occurring biocompatible materials which have been employed for bone prosthesis have also been employed for dental restorative purposes. In particular, calcium phosphates, such as hydroxylapatite, tricalcium phosphate (whitlockite) and mixtures thereof have been widely reported in the literature as suitable for use as bone prostheses as well as for dental restorative purposes. See, e.g. Monroe et al., *J.Dent.Res.* 50, pp. 860 et seq. (1971); Rao & Boehm, *J.Dent.Res.* 53, p. 1353 et seq. (1974); Bett et al., *J.A.C.S.* 89, p. 5335 et seq. (1967); Kutty, *Indian J.Chem.* 11, 695 (1973).

Hydroxylapatite is a naturally occurring mineral present in phosphate rock. Hydroxylapatite also constitutes the mineral portion of natural bone and tooth. As such it is highly biocompatible and has a thermal coefficient of expansion quite similar to tooth enamel.

As discussed in greater detail below, in accordance with the preferred embodiments of the method of this invention, fine dry particles of a hydroxylapatite powder are agglomerated with a binding agent into sinterable spheroidal agglomerates. The spheroidal agglomerates are then sintered to provide spheroidal ceramic particles of hydroxylapatite having a uniform network of micropores extending throughout the ceramic product.

U.S. Pat. No. 4,097,935 (hereinafter '935) sets forth a description of a method for preparing a maximally densified, pore-free hydroxylapatite ceramic body. In accordance with the '935 patent the dense, pore-free ceramic body described therein may be prepared by sintering (under specified conditions) a shaped body or mass prepared from an aqueous gelatinous precipitate of hydroxylapatite. The '935 patent teaches away from the use of both products and processes which employ fine particles of hydroxylapatite as starting materials in the preparation of the dense, pore-free ceramic products described in the '935 patent. In this regard the '935 patent states:

It is critical, in the above process, to prepare the hydroxylapatite as a gelatinous precipitate from aqueous solution for it is only in this cohesive gelatinous state that hydroxylapatite can be shaped or molded and then dried and sintered to produce a ceramic body. Dry particulate or granular hydroxylapatite cannot be reconstituted into the cohesive gelatinous state . . . Moreover although powdered hydroxylapatite can be compressed into a shaped body, such as a tablet, when sintered according to the method of this invention the product obtained is highly porous and does not fracture along smooth planes but simply shatters. (Col. 9, lns. 22-39).

In contrast to the foregoing the method of this invention employs dry particulate hydroxylapatite as the starting material in a novel method employed to prepare porous hydroxylapatite ceramic particles having a network of micropores extending throughout the ceramic product.

The '935 patent also discloses means for introducing pores into the ceramic bodies produced in accordance with the method described in that patent. In this regard the '935 patent states that pores may be introduced by drilling or machining holes in the non-porous ceramic product, or by mixing an organic binder with a body of the gelatinous hydroxylapatite precipitate prior to sintering. The binder is said to volatilize during sintering to produce pores in the ceramic product. The sintered body would then have to be ground, or comminuted in some other way to provide a particulate ceramic product.

Unlike the method described in the '935 patent, in accordance with applicant's method, a binding agent is not added to a gelatinous precipitate of hydroxylapatite, and in producing applicant's final ceramic it is not a sinterable body prepared by adding a binding agent to an aqueous gel which is ultimately sintered. Rather, contrary to the method described in the '935 patent, in accordance with applicant's method the binding agent is employed to agglomerate together fine dry particles of hydroxylapatite, and it is applicant's novel agglomerate of dry hydroxylapatite particles which is sintered in accordance with the method of the present application.

Biocompatible compositions suitable for use as a dental filling material have been prepared by mixing finely divided ceramics such as sintered hydroxylapatite with a hardenable binder material. In addition, moist ceramic particles of hydroxylapatite have been employed as a biocompatible packing material to fill the voids or lesions caused by advanced periodontal diseases. The ceramic particles used have typically been employed in the form of very finely divided ceramic powders made up of particles in the range of about 10 to about 60 mesh.

Fine particles of calcium phosphate ceramics suitable for use in such filling or packing compositions may be prepared by grinding larger particles or masses of the ceramic down to fine particles within the desired particle size range. The grinding step may be conducted before or after sintering. However, in order to obtain a ceramic powder made up of particles within a desired size range, particles larger and particles smaller than desired must be separated by sieving or by another particle classification process, from the mass of particles produced by the grinding step. Thus, grinding processes typically yield a fraction of ceramic particles which are smaller than the desired particle size range, and which are often simply discarded as waste. Moreover, the ceramic particles produced by grinding are typically not uniform in shape, and possess sharp edges or "points" which could lead to local inflammation when placed in contact with tissue.

Ground hydroxylapatite particles and other ceramic particles having sharp edges or points can be mechanically treated to render the particles substantially spheroidal in shape and smooth. However, such mechanical procedures involve extensive milling to remove the sharp edges from the ceramic particles. The process itself is very cumbersome, and the yields quite low.

Conventional molding, casting or pressing operations, which do not involve grinding or milling, are generally suitable for the preparation of smooth round ceramic particles. However, in the case of calcium phosphate and other ceramics intended for use in bone or tooth restorative compositions, particles on the order of 20-40 mesh are often desired, and such particles are too small to be produced by the conventional fabrication processes known to be useful to prepare round smooth particles.

It is an objective of this invention to provide a substantially waste-free, high-yield, ceramic particle-forming process which may be employed to prepare spheroidal particles which are substantially spheroidal in shape, and are within a desired particle size range.

It is a particular objective of this invention to provide a high-yield process for the preparation of biocompatible ceramic particles, especially particles of calcium phosphate and aluminum oxide ceramic which are substantially spheroidal in shape and within about the 10 to about 80 mesh range. The spheroidal ceramic particles produced by the process of this invention are free of sharp edges or ridges capable of producing local irritation when placed in contact with tissue. As such, the spheroidal ceramic particles of this invention are suitable for use as the ceramic component of hardenable binder compositions formulated for use for dental or bone restorative purposes.

BRIEF DESCRIPTION OF THE INVENTION

In accordance with the foregoing, this invention provides a high-yield method for preparing sintered ceramic particles which comprises the steps of binding together fine particles of a sinterable inorganic powder to provide sinterable particulate agglomerates within a desired size range. The fine particles of the sinterable powder may be bound together to form the agglomerate by an organic binding agent, such as a starch or another polymeric adhesive. The agglomerate may then be sintered to provide the final particulate ceramic product.

In the preferred embodiments of the method of this invention, fine particles of sinterable hydroxylapatite and/or whitlockite are agglomerated together with an organic binding agent to provide sinterable agglomerates which are spheroidal in shape. If desired, the agglomerate may be subjected to elevated temperatures in order to eliminate the binder from the agglomerate prior to subjecting the agglomerate to higher temperatures in order to complete the sintering process.

It has been found that when the calcium phosphate (e.g. hydroxylapatite and/or tricalcium phosphate) based agglomerate of this invention is sintered at elevated temperatures, the individual inorganic particles which comprise the agglomerate meld together to provide a strong, free-flowing, structurally stable ceramic particle. In addition, the finally sintered agglomerate includes a network of micropores extending throughout the particle. Advantageously, the microporous structure of the particle provides sites for tissue ingrowth and attachement, while the smooth surface of the particles prevents the inflammatory response noted in connection with the rough and irregular surfaces of untreated ground ceramics.

In addition to the advantages mentioned above, the ceramic particle-forming process of the invention may be conducted such that only a minor amount of the finely powdered ceramic starting material is wasted. In accordance with the process of this invention, agglomerates which are smaller than desired, or any starting ceramic powder which is not agglomerated, may be reused in a subsequent agglomerating process. Similarly, agglomerates which are larger than desired may simply be re-ground and used in a subsequent agglomerating process.

DETAILED DESCRIPTION OF THE INVENTION

In accordance with the first step of the process of this invention, sinterable agglomerates are prepared by adhering together fine particles of a sinterable powder with a binding agent or adhesive. The initial particle size of the fine sinterable powder starting material employed to form the agglomerate is preferably in the range of about 1 to about 75 microns, and most preferably in the range of about 5 to about 50 microns. The fine sinterable powder may be prepared by conventional methods, such as by grinding or milling larger particles or masses of a sinterable material. However, as described in greater detail below, it is preferred to prepare the finely divided ceramic powder by a spray-drying process. Spray-drying is preferred because it provides a better than 90% yield, provides particles within a narrow particle size range, and provides an easy-to-handle, free-flowing powder.

The binding agent employed to agglomerate the sinterable particles may be any material capable of adhering the particles of the starting powder together, and which decomposes without leaving undesirable residues when subjected to elevated temperatures. The preferred binding agents for use herein include organic binders, for example, starches (especially pregelatinized starch, polyvinyl alcohol and polyvinyl pyrrolidone).

The sinterable agglomerate may be prepared by applying the binding agent (or a solution of the binder) to a fluidized bed of the ceramic powder. For example, dry and finely ground hydroxylapatite powder may be charged into a Glatt Powder Coater, Model No. GPCG 5-9 (manufactured by Glatt-Air Technique, Inc. of Ramsey, N.J.) which fluidizes and agitates the powder particles, while the binder is fed at a controlled rate onto the fluidized bed of particles. In the Glatt Powder Coater the fine powder is fluidized by the introduction of a stream or jet of air into the device which "puffs up" the powder particles and suspends them in air. At the same time the powder is agitated in a rotary fashion in the Powder Coater. When the binding agent is sprayed onto the rotating, fluidized bed, the powder particles agglomerate into larger and larger sized agglomerates in a snowball-like fashion, as the amount of binder added to the bed increases. The resultant agglomerates are substantially spheroidal in shape.

As an alternative to spraying the binder onto the fluidized bed of fine sinterable particles, the binder may be added as a solid dispersed within the fluidized bed of fine sinterable particles. In this embodiment of the process, the fluidized bed of the initially added sinterable particles and binder may be sprayed with a suitable liquid, for example, water or an aqueous solution of the binder.

For example, following the techniques discussed above, hydroxylapatite powder, having a particle size in the range of about 1 to about 75 microns, may be agglomerated with an organic binder until agglomerates in about the 10 to about 80, preferably about 20 to about 70 mesh range, are formed. The sintered ceramic is typically somewhat smaller in size than the agglomerate from which it is prepared. Thus, it is preferred to sinter agglomerates within a particle size range wherein the largest agglomerates are about 15-75% larger, preferably about 30% larger, than the largest ceramic particle desired; while the smallest agglomerates are also about 15-75% larger, preferably about 30% larger, than the smallest ceramic particles desired. Thus, prior to sintering, it is preferred to classify the group of particles which are produced by the agglomeration step in order to select agglomerated particles within the appropriate particle size range. The classification of particles may be conducted by sieving, or by any other conventional sorting or particle classification technique.

One of the advantages of the process of this invention is that off-sized agglomerates or any non-agglomerated starting material may be recycled. That is, agglomerated particles which are smaller than desired can simply be reused in a later batch, while agglomerates that are too large may be ground to a smaller size, and reused during a subsequent agglomeration process. Thus, there should be little or no waste resulting from the agglomeration process. Moreover, as shown by the following Examples, the sintering process may yield 90% or more of sintered ceramic particles within the desired particle size range.

In further embodiments of the method of this invention, the agglomerated particles produced in the manner described above may be employed as core or seed particles in a second agglomeration process. During the second agglomeration process, the previously prepared core particle, which is itself an agglomerate, may be coated with additional layers of binder plus additional fine ceramic particles. Through this embodiment of the method of this invention, one can prepare a sinterable agglomerate made up of a core of one ceramic material, over which a plurality of spheroidal shells or layers of the same or a different ceramic material are formed. Through this embodiment one may also prepare a sinterable agglomerate of hydroxylapatite made up of a core of a given density over which one or a plurality of shells or layers may be formed having a different density than the core agglomerate. A shell or layer may also be applied to the core particle which is made up of an hydroxylapatite having a particle size which is different from the hydroxylapatite particles which make up the core of the sinterable agglomerate.

The sinterable agglomerates of this invention preferably are comprised of about 10% to about 25% by weight of the binder, preferably about 10% to about 15% of the binder, while the agglomerate preferably comprises about 75% to about 90%, and preferably about 85% to about 90% by weight of sinterable ceramic particles of hydroxylapatite, and/or whitlockite or aluminum oxide. Moreover, the bulk density of the agglomerate is preferably about 0.8 to about 1.5 grams/cc, for agglomerates within about the 10 to about 80 mesh range, while for the preferred agglomerates of hydroxylapatite, the bulk density is about 1 to about 1.2 grams/cc for agglomerates in about the 15 to about 30 mesh range.

It should be noted that the sinterable powder employed to form the agglomerate may be in the form of irregularly shaped particles which possess microscopic ridges or points. When these very fine particles are agglomerated into the larger agglomerates (typically in about the 10-80 mesh range) and then sintered, the larger sintered ceramic particle possesses a macroscopically smooth surface. In contrast, ceramic particles in the 10-80 mesh range prepared, for example, by grinding larger ceramic particles possess larger surface points or ridges. It is the larger ridges or points of the ground ceramic materials which present a danger of local irritation when such ceramics are placed in contact with tissue.

The agglomerates of this invention are sintered to provide the finished particulate ceramic product. The temperature and duration employed to sinter the agglomerate may be the same as those one would conventionally employ to sinter the sinterable powder from which the agglomerate was prepared. Preferably, however, the agglomerate is slowly heated up to sintering temperatures such that the binder is eliminated before the agglomerate reaches the more elevated sintering temperatures. If the agglomerate is rapidly heated to sintering temperatures, there is a danger that the binding agent will carbonize and produce a dark off-color in the ceramic product.

In embodiments of the method of this invention, the hydroxylapatite-containing agglomerate is subjected to a preliminary heat treatment at a temperature sufficient to eliminate the binder from the agglomerate without producing a carbonized residue. This preliminary heat treatment is preferably conducted at temperatures below about 700° C., and most preferably below about 650° C. However, the actual temperature employed will be a function of the particular binder selected, air flow in the oven, etc. It has been found that the foregoing heat treatment serves to eliminate the binder while nevertheless providing a structurally-stable, binder-free agglomerate of hydroxylapatite. The binder-free agglomerate of hydroxylapatite particles may then be subjected to elevated sintering temperatures without fear of discolorization of the product due to carbonization of the binder. The resultant ceramic particle preferably has a white color.

For the preferred agglomerate of hydroxylapatite powder, sintering is conducted at a temperature of about 1100° C. to 1300° C. for about 1 to about 5 hours, most preferably at about 1150° C. to 1250° C. for about 1 to about 3 hours. If desired, the temperature and/or duration of sintering may be adjusted to convert a portion or all of the hydroxylapatite present in the agglomerate into tricalcium phosphate as a by-product of the sintering process.

Fine sinterable hydroxylapatite powder suitable for agglomeration may be prepared by any conventional granulating and/or particle sorting technique. Preferably, however, the fine particulate hydroxylapatite starting material employed herein is prepared by first preparing a gelatinous aqueous precipitate of hydroxylapatite, and then processing the precipitate into a sinterable fine dry powder suitable for use in the agglomeration process.

A suitable procedure for the preparation of an aqueous gel of hydroxylapatite is described by E. Hayek et al., *Inorganic Synthesis*, 7, 63 (1963) which is incorporated herein by reference. Hayek et al. disclose the precipitation of hydroxylapatite using phosphate solution, in accordance with the following reaction scheme:

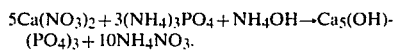

$$5Ca(NO_3)_2 + 3(NH_4)_3PO_4 + NH_4OH \rightarrow Ca_5(OH)(PO_4)_3 + 10NH_4NO_3.$$

The reaction disclosed by Hayek et al. leads to a gelatinous precipitate of hydroxylapatite which must be maintained in contact with the original solution or mother liquor until the molar ratio of calcium to phosphorus in the precipitate reaches the stoichiometric proportions characteristic of hydroxylapatite, i.e., 5:3 or 1.67.

Once the stoichiometric proportions of calcium and phosphorus characteristic of hydroxylapatite are obtained, the gelatinous precipitate is separated from the mother liquor, and the precipitate is washed to substantially reduce or, if desired, to eliminate the ammonium nitrate present in the gelatinous product. Since ammonium nitrate decomposes into gaseous by-products at temperatures of about 180° C. to about 300° C., the generation of gas from ammonium nitrate during the heating of the agglomerate can lead to a breakup or weakening of the agglomerated hydroxylapatite particle. Ammonium nitrate may conveniently be removed, or at least substantially eliminated, from the gelatinous hydroxylapatite precipitate by re-suspending the precipitate in water, centrifuging the suspension, and then decanting the water.

The gelatinous precipitate of hydroxylapatite is next dried and converted into fine particles. The foregoing may be accomplished by way of a number of different drying or granulating techniques. Drying techniques which can be used include, for example, tray drying vacuum drying, etc. If desired, the dried particles may be ground and then classified in order to obtain particles within the desired particle range.

Spray drying is the preferred technique for converting the gelatinous precipitate of hydroxylapatite into the fine dry particles suitable for use in the agglomeration process. The gelatinous precipitate may be spray dried by first preparing an aqueous slurry of the precipitate suitable for spray drying. The slurry may have a solids content of about 5% to about 15%, preferably about 7% to about 10% by weight, and the slurry may then be spray dried to provide particles within the desired size range.

Spray drying may be conducted at temperatures of less than 400° C., e.g., in a conventional spray dryer employing an air inlet temperature of about 250° C., and an outlet temperature of about 115° C. Under these conditions the finally spray-dried hydroxylapatite particles are in a substantially anhydrous state, and the hydroxylapatite is no longer gelatinous, but may contain some chemically bound water. The spray-dried product obtained is in the form of dry porous particles of hydroxylapatite which cannot be reconstituted into the gelatinous state by the addition of water. Moreover, the spray-dried particles of hydroxylapatite are substantially spheroidal in shape.

The finally sintered hydroxylapatite agglomerates of this invention preferably have a porosity sufficient to permit the desired degree of tissue ingrowth to ensure proper attachment when the ceramic is employed for prosthetic purposes or as an implant material. The preferred ceramic hydroxylapatite ceramic produced in accordance with this invention is substantially spheroidal in shape and has a bulk particle density of about 80% to about 95% of the theoretical maximum density of pure hydroxylapatite. Moreover, the ceramic hydroxylapatite product includes an extensive network of micropores extending throughout the product, as seen by Scanning Electron Microscopic analysis. The individual pores which form the network are preferably all less than about 40 to about 50 microns (maximum pore diameter) in size. Most preferably, the median pore size is about 1.5 microns as determined by mercury poresimetry, with about 90% of the pores being less than about 0.3 microns.

In further aspects of this invention, the finely sintered ceramic particles produced by the method of this invention may be combined with an orally compatible binder material and employed as a dental restorative material used to fill lesions caused by periodontal disease, or to augment or restore the alveolar ridge. The dental restorative compostions may also be employed as a tooth filling material, a dental liner, to mold or cast artifical teeth, etc. The spheroidal ceramic particles of this invention which employ pure hydroxylapatite are preferred for use in such dental restorative compositions because hydroxylapatite possesses a thermal coefficient of expansion substantially identical to that of natural tooth enamel, the hardness of hydroxylapatite is similar to the hardness of natural tooth, and in addition natural tooth and hydroxylapatite stain in a similar way.

The preferred dental restorative compositions of this invention are comprised of about 5% up to about 90% by weight of the hydroxylapatite cermic of this invention dispersed within about 10% to about 95% by weight of an orally compatible binder.

Suitable binders for use in the preparation of the dental restorative materials of this invention, and particularly those employed to augment or restore the alveolar ridge, or to fill periodontal lesions, include inorganic binders such as a binder comprised of plaster of pairs (calcium sulfate hemihydrate) and water. Alternative binding materials include polymeric or polymerizable materials in combination with the appropriate additives for hardening the binder, e.g., crosslinking agents, polymerization catalysts, diluents, etc.

The polymeric or polymerizable binder may be selected from a broad group of known polymeric materials suitable for use in the oral cavity. Such materials include, for example, polymethacrylates such as hydroxylethylmethacrylate, polymethylmethacrylate, as well as other polyacrylic acids or esters, epoxy resins, polyesters, etc.

In addition, the ceramic particles produced in accordance with this invention may be admixed with a biocompatible inorganic or organic binder, and then cast or molded into the form of a tooth, bone, a portion of a bone, etc. Bone prosthesis prepared in this manner may then be surgically implanted employing conventional surgical techniques.

The spheroidal ceramic hydroxylapatite of this invention is also particularly well suited for use as a surgical implant material. For example, moist spheroidal particles of the hydroxylapatite ceramic in the size range of about 10 to 60 mesh may be used to fill properly prepared lesions caused by periodontal diseases. The moist hydroxylapatite is packed into the lesion following known periodontal procedures. In addition, the ceramic hydroxylapatite ceramic of this invention may be diluted with a biocompatible diluent such as saline solutions or even blood, and injected into or about the alveolar ridge in order to augment or restore portions of that ridge, in accordance with known surgical procedures. For this purpose the spheroidal hydroxylapatite ceramic is preferably in about the 10 to about 60 mesh range.

When surgically filling or packing a periodontal lesion or another undesired void with the ceramic particles of this invention, it is desirable to completely fill the void. Advantageously, when a periodontal lesion or another void is packed with spheroidal ceramics of this invention, the ceramic filling substantially retains its original volume with little or no reduction in the volume of the filling material due to the settling of the particles in the void. In contrast, irregularly shaped non-spheroidal particles tend to settle in a void causing an undesired reduction in the volume of the filling material.

This invention will be described further with reference to the following detailed Examples.

EXAMPLE 1

45.4 kg of calcium nitrate tetrahydrate was dissolved in 265 liters of deionized water and 62 kg of 26% ammonia water was added.

Separately, 15.2 kg of ammonium phosphate dibasic was dissolved in 378 liters of water and 28 kg of 26% ammonia was added. This solution was added into the solution of calcium nitrate under agitation which was then continued for 36 hours at ambient temperature. The slurry was then centrifuged through a split bowl centrifuge (Centrico, Inc. Model SB7). The solids were collected, dispersed in 500 liters of D.I. water and centrifuged again, dispersed once more in 500 liters of D.I. water and centrifuged. The collected solid was dried in a vacuum tray dryer at 80° C. and 60 mm Hg pressure. Dry hard white lumps thus obtained were ground in the hammermill to pass an 80 mesh screen.

Yield: 18.90 kg of $Ca_5(OH)(PO_4)_3$—97.9%

EXAMPLE 2

45.4 kg of the calcium nitrate was precipitated with ammonium phosphate exactly as described in Example 1. The precipitate was centrifuged and twice redispersed in 500 liters of D.I. water and centrifuged again. The gelatinous solid was dispersed in D.I. water again to produce a slurry with 8.3% of solids which was then spray dried using Bowen spray dryer:

| air inlet temperature: | 250° C. |
|---|---|
| air outlet temperature: | 115° C. |

The product was obtained as a white powder of the particle size 20–40 microns in the main fraction.

Yield: 17.60 kg of $Ca_5(OH)(PO_4)_3$—91.1%

EXAMPLE 3

4.0 kg of hydroxylapatite powder prepared as described in Example 1 was charged into Glatt powder coater/granulator GPCG 5-9.

400 g of pregelatinized starch was dissolved in 4600 g of D.I. water.

The rotor was turned on and speed adjusted at 400 rpm, the air jet temperature was 70° C. and starch solution was sprayed-in initially at 120 g/min., and later at 40 g/min. High initial flow rate is necessary to prevent loss of the dry fine powder. Agglomeration was monitored by sieving samples taken in approximately 5 min. intervals. Feeding of the starch solution was disconcontinued when the desired particle size was reached (approx. 60 min.); material was dried, discharged and sieved.

| Yield: 4.45 kg -- 96.7% | | |
|---|---|---|
| Sieve Analysis: | +16 mesh | 5.8% |
| | 16–30 mesh | 54.7% |
| | −30 mesh | 39.5% |

The fraction 16–30 mesh—2.43 kg—was charged into alumina crucibles and sintered; the material was heated to the temperature 1200° C. at the rate of 8° C./min., temperature 1200° C. was maintained 2 hours, material was cooled down to 300° C. and removed from the furnace at this temperature. Product was weighed and sieved again.

| Yield: | 2.17 kg | 89.3% |
|---|---|---|
| Sieve Analysis | 16–20 mesh | 3.8% |
| | 20–40 mesh | 93.5% |
| | −40 mesh | 2.7% |

EXAMPLE 4

5.0 kg of spray dried hydroxylapatite powder, prepared as described in Example 2, was charged into the Glatt GPCG 5-9 granulator.

400 g of pregelatinized starch was dissolved in 4600 g of D.I. water. The rotor was turned on at 400 rpm and starch solution washed in at 120 g/min initially, and later at a rate of 40–60 g/min. Feeding of the starch solution was discontinued when the desired particle size was reached. The material was then dried and discharged.

| Yield: | 4.55 g | 91.-% |
|---|---|---|
| Sieve Analysis: | +16 mesh | 6.7% |
| | 16–30 mesh | 61.3% |
| | −30 mesh | 32.0% |

The fraction 16–30 mesh—2.79 kg—was sintered as described in Example 3.

| Yield: | 2.63 kg | 94.3% |
|---|---|---|
| Sieve Analysis | 16–20 mesh | 4.7% |
| | 20–40 mesh | 91.5% |
| | −40 mesh | 3.8% |

EXAMPLE 5

5.0 kg of spray dried hydroxylapatite powder, prepared as described in Example 2, was charged into a Glatt GPCG 5-9 granulator.

1.00 kg of polyvinylpyrrolidone K29-32 was dissolved in 4 liters of D.I. water. The rotor was turned on at 400 rpm and the binder solution was fed in at 120 g/min. initially and later at 40-60 g/min. Feeding was discontinued when the desired particle size was reached. The material was then dried and discharged.

| Yield: | 4.65 kg | 93.0% |
|---|---|---|
| Sieve Analysis: | +16 mesh | 16.3% |
| | 16-30 mesh | 73.5% |
| | −30 mesh | 10.2% |

The fraction 16-30 mesh—3.42 kg—was sintered as described in Example 3.

| Yield: | 3.23 kg | 94.4% |
|---|---|---|
| Sieve Analysis: | 16-20 mesh | 4.1% |
| | 20-40 mesh | 93.1% |
| | −40 mesh | 2.8% |

EXAMPLE 6

4.0 kg of the spray dried hydroxylapatite was preagglomerated to the particle size 40-60 mesh.

400 g of the pregelatinized starch was dissolved in 4600 g of D.I. water.

8.0 kg of the spray dried hydroxylapatite of particle size 20-4 microns was charged into powder coating injection port.

Rotor was turned on at 400 rpm speed, starch feeding at 80 g/min. and the powder injection was set for 8.0 kg/hr. Agglomeration of particles 40-60 mesh and coating of this preagglomerate took place simultaneously. The particle size 14-25 mesh was reached within 54 minutes. At this point the speed of the rotor was increased to 900 rpm, feeding of the powder and starch was discontinued, heating was stopped and material was sprayed with D.I. water for 10 minutes. Higher speed compacted the particles and increased their density and the particle size shrunk to the desired 16-30 mesh. The rotor speed was brought down to 400 rpm, water spraying was discontinued and material was dried.

| Yield: | 11.34 kg | 94.5% |
|---|---|---|
| Sieve Analysis: | +16 mesh | 7.1% |
| | 16-30 mesh | 92.3% |
| | −30 mesh | 0.6% |

The fraction 16-30 mesh—10.47 kg—was sintered as described in Example 3.

| Yield: | 9.69 kg | 92.5% |
|---|---|---|
| Sieve Analysis: | 16-20 mesh | 5.7% |
| | 20-40 mesh | 92.9% |
| | −40 mesh | 1.4% |

EXAMPLE 7

5.1 kg of the off size, granulated hydroxylapatite of particle size +16 mesh and −30 mesh was ground in the hammermill to the particle size −80 mesh and charged into the Glatt GPCG 5-9 granulator. This material was a leftover from agglomeration as described in Example 4; and as such, it contained starch used in the agglomeration.

400 g of pregelatinized starch was dissolved in 4600 g of water.

Rotor was turned on at 400 rpm speed and starch feeding started at 80 g/min. Agglomeration begain within 10 minutes and the desired particle size 16-30 mesh was reached in 35 minutes. Faster response was due to the starch content in the starting material. The material was dried and discharged.

| Yield: | 4.90 kg | 96.1% |
|---|---|---|
| Sieve Analysis: | +16 mesh | 6.9% |
| | 16-30 mesh | 90.8% |
| | −30 mesh | 2.3% |

The fraction 16-30 mesh—4.45 kg—was sintered as described in Example 3.

| Yield: | 4.13 kg | 92.8% |
|---|---|---|
| Sieve Analysis: | 16-20 mesh | 6.1% |
| | 20-40 mesh | 90.9% |
| | −40 mesh | 3.0% |

EXAMPLE 8

5.0 kg of the spray dried hydroxylapatite and 400 grams of pregelatinized starch were charged into the Glatt GPCG 5-9 granulator.

Rotor was turned on at 400 rpm speed and the fluidized powder was sprayed with D.I. water at the rate of 80 g/min. initially and at 40 g/min. rate later. Powder was gradually agglomerated and the spray of the water was discontinued when the main fraction reached the size 16-30 mesh. Material was dried and discharged.

| Yield: | 5.2 kg | 96.3% |
|---|---|---|
| Sieve Analysis: | +16 mesh | 5.7% |
| | 16-30 mesh | 90.9% |
| | −30 mesh | 3.4% |

The fraction 16-30 mesh—4.73 kg—was sintered as described in Example 3.

| Yield: | 4.38 kg | 92.6% |
|---|---|---|
| Sieve Analysis: | 16-20 mesh | 2.8% |
| | 20-40 mesh | 93.7% |
| | −40 mesh | 3.5% |

EXAMPLE 9

5.0 kg of the agglomerated hydroxylapatite of the particle size 20-30 mesh was charged into the Glatt GPCG 5-9 granulator with a Wurster column insert.

Sludge of the hydroxylapatite was prepared as described in Example 2, redispersed in D.I. water and centrifuged again twice and diluted with D.I. water to contain 7% solids.

40 kg of this sludge was weighed; 300 g of pregelatinized starch was added and dissolved in the sludge and this mixture was then sprayed on the fluidized bed of the granulated hydroxylapatite in the Wurster column at the flow rate 40-60 g/min. The product was dried, discharged and sieved.

| Yield: | 7.72 kg | 91.0% |
| --- | --- | --- |
| Sieve Analysis: | +16 mesh | 4.1% |
| | 16-30 mesh | 95.4% |
| | -30 mesh | 0.5% |

The fraction 16-30 mesh—7.36 kg—was sintered as described in Example 3.

| Yield: | 6.92 kg | 94.0% |
| --- | --- | --- |
| Sieve Analysis: | 16-20 mesh | 11.1% |
| | 20-40 mesh | 88.1% |
| | -80 mesh | 0.8% |

What is claimed is:

1. Ceramic particles of a calcium phosphate material suitable as an implant or prosthesis material, characterized by a bulk density between about 80% and about 95% of the theoretical bulk density of the calcium phosphate material, a size range of between 10 and 80 mesh, and a network of micropores in the individual particles sufficient to permit tissue attachment when the particles are employed as an implant or prosthesis material wherein said micropores have a medium pore size of about 1.5 microns as determined by mercury porosimetry.

2. Ceramic particles as in claim 1 wherein said micropores have a maximum pore diameter of 50 microns.

3. Ceramic particles as in claim 1 wherein about 90% of the pores are less than about 0.3 microns in diameter.

4. Ceramic particles as in claim 1 wherein the calcium phosphate material is selected from the group consisting of hydroxylapatite, tricalcium phosphate, and mixtures thereof.

5. Ceramic particles as in claim 4 wherein said calcium phosphate material is substantially 100% hydroxylapatite.

6. Ceramic particles as in claim 1 wherein the particles are in the 10-60 mesh range.

7. Ceramic particles as in claim 1 further characterized by a substantially spheroidal shape.

8. A sinterable agglomerate comprised of individual dry particles of a sinterable calcium phosphate material adhered together with an organic binder, said agglomerate having: a substantially spheroidal shape; a particle size of about 10-80 mesh; and a bulk density of about 0.8 to about 1.2 grams/cc.

9. A sinterable agglomerate as in claim 8 wherein said calcium phosphate material is substantially 100% hydroxylapatite.

10. A sinterable agglomerate as in claim 9 wherein said individual dry particles are in the size range of 10-80 mesh.

11. The sinterable agglomerate according to claim 10 wherein said binding agent is selected from the group consisting of polyvinyl alcohol, starch, and polyvinyl pyrrolidone.

12. A method of preparing an implantable calcium phosphate particulate material in the size range of 10-80 mesh comprising:
(a) agglomerating together dry particles of a sinterable biocompatible calcium phosphate material in the size range of about 1 to about 75 microns with a binding agent to provide sinterable substantially spheroidal agglomerates having a size range of about 15-75% larger than the desired size range of the sintered particles; and
(b) sintering the agglomerates to provide said sintered ceramic particles characterized by a substantially spheroidal shape and a network of micropores extending throughout each individual particles, said network of micropores sufficient to permit tissue attachment when the particles are employed as an implant.

13. The method of claim 12 wherein the calcium phosphate material comprises hydroxylapatite.

14. The method of claim 13 wherein said sintering step is performed at a temperature of about 1100°-1300° C.

15. The method of claim 12 wherein said dry particles of sinterable calcium phosphate are prepared by spray drying an aqueous gelatinous precipitate of hydroxylapatite, tricalcium phosphate or mixtures thereof to provide a fine dry powder in the size range of about 1-75 microns.

16. The method of claim 15 wherein the gelatinous precipitate is adjusted to a solids content of about 5% to about 15% by weight prior to spray drying.

* * * * *

UNITED STATES PATENT AND TRADEMARK OFFICE
CERTIFICATE OF CORRECTION

PATENT NO. : 4,693,986

DATED : September 15, 1987

INVENTOR(S) : Vit et al

It is certified that error appears in the above-identified patent and that said Letters Patent is hereby corrected as shown below:

On the title page

Inventor's name: Jaroslay should be Jaroslav

IN THE SPECIFICATON

Column 8, line 32 "artifical" to --artificial--.

Column 8, line 43 change "cermic" to --ceramic--.

Column 11, line 33 change "20-4" to --20-40--.

Signed and Sealed this

Fifth Day of July, 1988

*Attest:*

DONALD J. QUIGG

*Attesting Officer*  *Commissioner of Patents and Trademarks*

UNITED STATES PATENT AND TRADEMARK OFFICE

Certificate

Patent No. 4,693,986                                                                          Patented: Sept. 15, 1987

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is:
Jaroslav Vit and Don J. Henderson.

Signed and Sealed this Third Day of July, 1990.

WILLIAM R. DIXON, JR.

*Supervisory Primary Examiner*
*Patent Examining Group 110*